United States Patent [19]

Prince et al.

[11] 4,118,479
[45] Oct. 3, 1978

[54] VACCINE FOR ACTIVE IMMUNIZATION CONTAINING HEPATITIS B SURFACE ANTIGEN AND ASSOCIATED ANTIGEN

[75] Inventors: Alfred M. Prince, Stamford, Conn.; John Vnek, Bronx; Robert A. Neurath, New York, both of N.Y.; Christian Trepo, Bron, France

[73] Assignee: The New York Blood Center, Inc., New York, N.Y.

[21] Appl. No.: 631,961

[22] Filed: Nov. 17, 1975

[30] Foreign Application Priority Data

Mar. 14, 1975 [FR] France .................. 75 08046

[51] Int. Cl.² .................................. A61K 39/12
[52] U.S. Cl. ............................................ 424/89
[58] Field of Search ................................. 424/89

[56] References Cited

U.S. PATENT DOCUMENTS

| 3,838,144 | 9/1974 | Leach | 424/89 |
| 3,951,937 | 4/1976 | Vnek | 424/89 |
| 3,976,767 | 8/1976 | Neurath | 424/89 |

OTHER PUBLICATIONS

Almeida–Lab–Lore, vol. 16, No. 6, Feb. 1975.

*Primary Examiner*—Sam Rosen
*Attorney, Agent, or Firm*—Burgess, Dinklage & Sprung

[57] ABSTRACT

A vaccine against viral heptitis comprising:
A. Antigenic particles having a particle size in the range of 30 to 50 nanometers, said antigenic particles containing heptitis B surface antigens;
B. Said antigen having less than 10 units of free antibody to hepatitis B surface antigens per 1,000 units of hepatitis B surface antigens;
C. At least 5% of the particles of said vaccine in the size range of 30 to 50 nanometers containing the hepatitis B surface antigenic specificity(s) which have been termed "e-antigen";
D. Said heptatis B surface antigens, including e-antigens, being present in said vaccine in an amount sufficient to produce antibodies when introduced into a host animal, the balance being a medium which is physiologically acceptable, especially to humans and primates.

15 Claims, 15 Drawing Figures

CELLULOSE ACETATE ELECTROPHORESIS OF FRACTION OF HBsAg/e
PURIFIED BY COLUMN CHROMATOGRAPHY ON HYDROXYLAPATITE I

COLUMN CHROMATOGRAPHY OF HBsAg/e ON HYDROXYLAPATITE III

FIG.8
IMMUNOELECTROPHORESIS OF FRACTIONS OF HBsAg/e
ELUTED FROM HYDROXYLAPATITE III
(1) Pool I
(2) Pool II
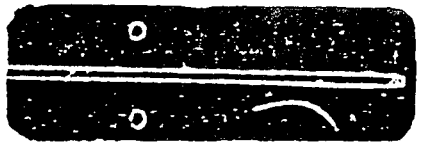
(3) Pool III
(4) Pool IV
(5) Pool V
(6) Pool VI
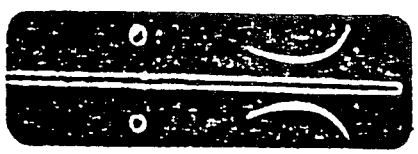
(7) Pool VII-VIII

FIG. 10
POLYACRYLAMIDE GEL ELECTROPHORESIS OF PURIFIED PREPARATIONS OF HBsAg/e SCHIFF BASE STAINING
A: 20-22 nm Spherical Particles
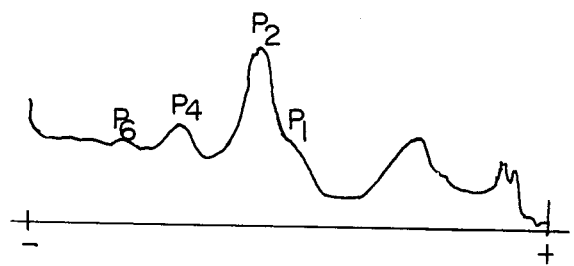
B: 22-28 nm Spherical Particles
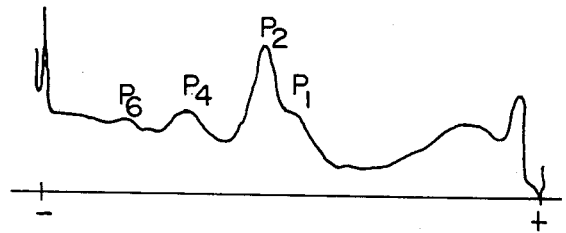

ELECTRON MICROSCOPY OF FRACTIONS OF HBsAg/e PURIFIED BY
BATCHWISE ELUTION FROM HYDROXYLAPATITE AND RATE ZONAL CENTRIFUGATION
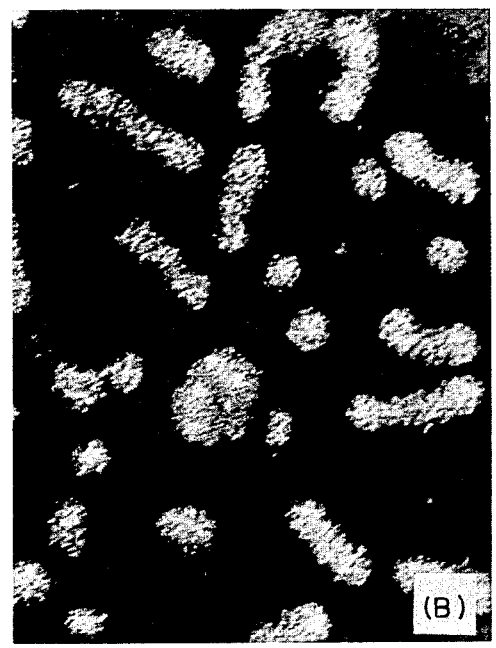
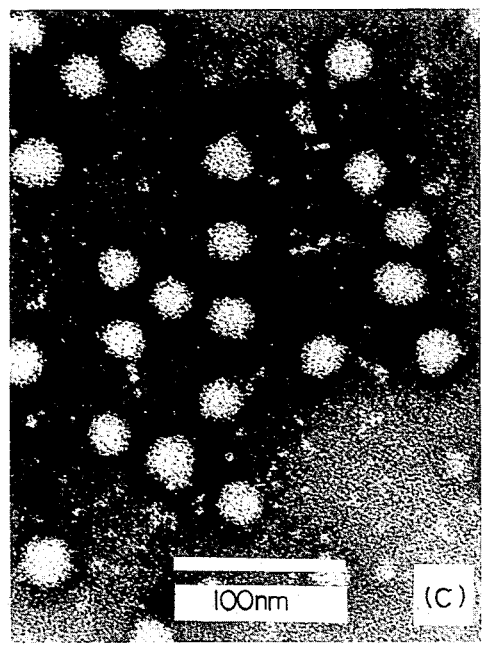
FIG. II

FIG.12A: THIN-LAYER ISOELECTRIC FOCUSING OF HBsAg/e
POOL I: 22-28 nm SPHERICAL PARTICLES
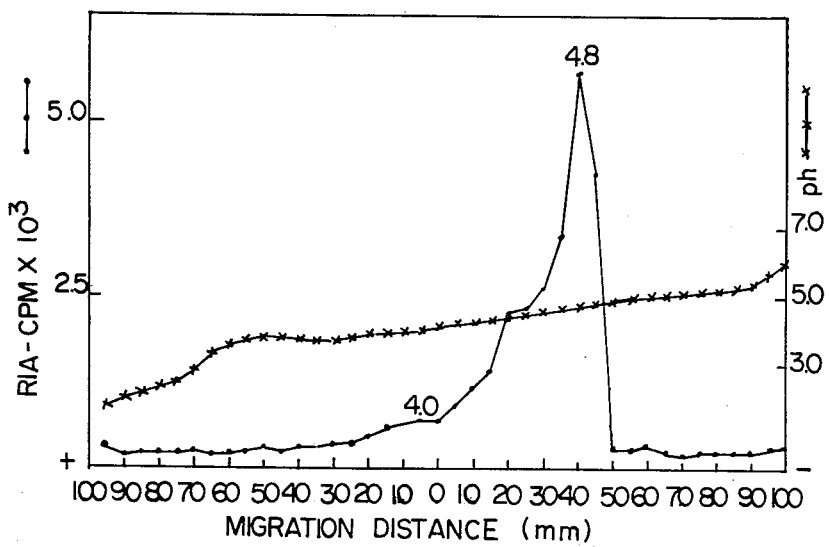
FIG.12B: THIN-LAYER ISOELECTRIC FOCUSING OF HBsAg/e
POOL II: 22-28 nm SPHERICAL PARTICLES, FILAMENTS AND DANE PARTICLES
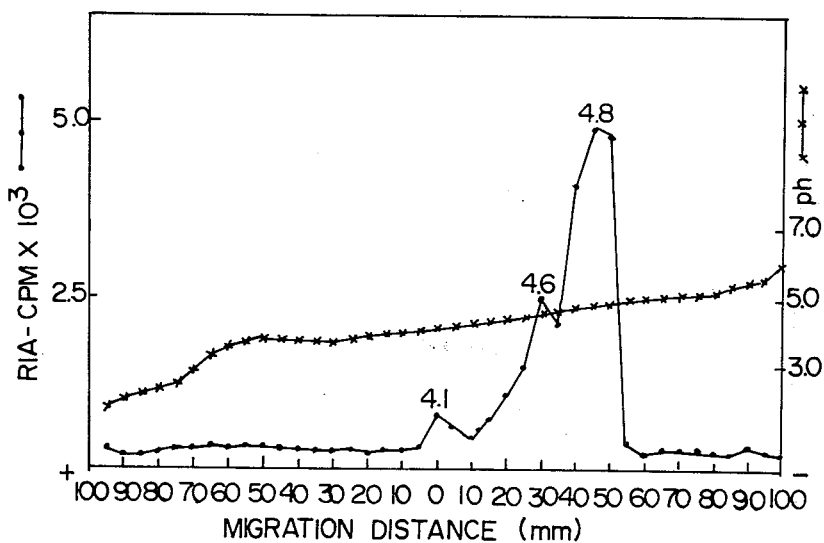

FIG. 13A: THIN-LAYER ISOELECTRIC FOCUSING OF TRITON X-100 TREATED HBsAg/e POOL I: 22-28 nm SPHERICAL PARTICLES
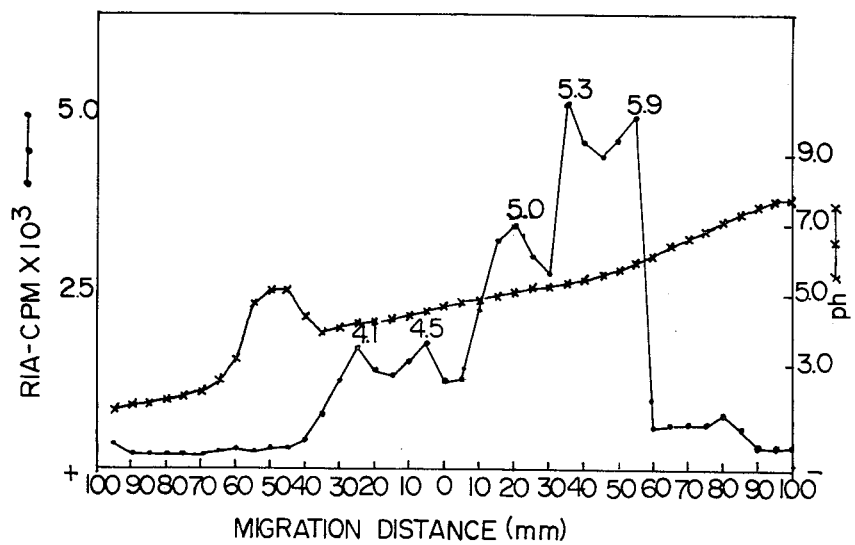
FIG. 13B: THIN-LAYER ISOELECTRIC FOCUSING OF TRITON X-100 TREATED HBsAg/e POOL II: 22-28 nm SPHERICAL PARTICLES, FILAMENTS AND DANE PARTICLES.
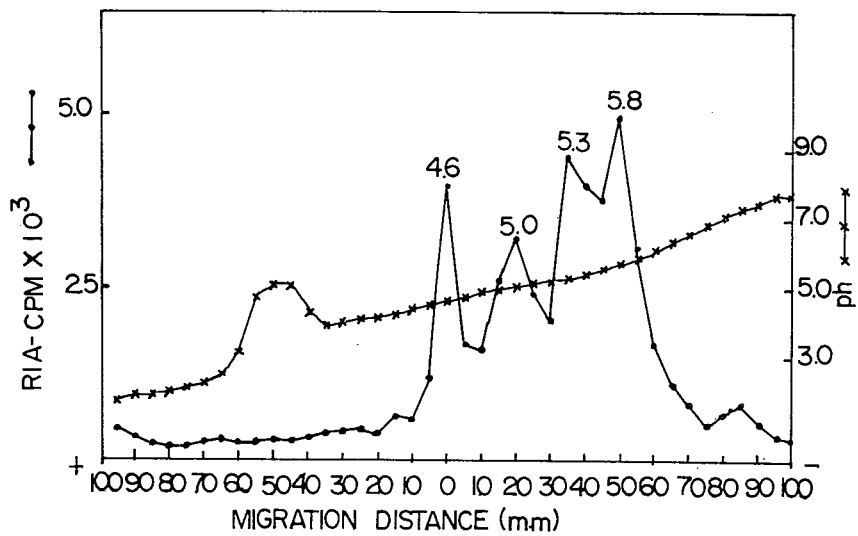

VACCINE FOR ACTIVE IMMUNIZATION CONTAINING HEPATITIS B SURFACE ANTIGEN AND ASSOCIATED ANTIGEN

ACKNOWLEDGMENT OF H.E.W. SUPPORT

The invention described herein was made in the course of or under a grant from the National Institute of Health, Department of Health, Education and Welfare.

BACKGROUND OF THE INVENTION

1. Field of the Invention

This invention relates to an effective vaccine against viral hepatitis which is characterized by containing large particles of filamentous and/or Dane particles characterized by a particle size of 20 to 50 nanometers (nm) said vaccine being further characterized by the substantial absence of antibodies to the antigens therein, the vaccine having both hepatitis B surface antigens as well as antigens which are specific for the virion itself such as e-antigen(s). The invention is also directed to the preparation of such vaccine, its purification and the multiplication of the vaccine in a host animal and the use thereof in active immunization against various forms of viral hepatitis.

2. Discussion of the Prior Art

Epidemiologic and human volunteer studies carried out between 1939 and 1967 prove the existence of two major hepatitis viruses — virus A and virus B. It became increasingly clear that further understanding of the virology of these viruses and the prevention of the diseases require the development of immunologic methodology. Considerable research focused on these viruses, particularly that known as virus B. Virus B was associated with those patients who had undergone a number of injections or transfusion of blood and, hence, the virus became known as serum hepatitis. As a result of the discovery of antigens specific for hepatitis B virus infections [Prince et al., Am. J. Hyg. 79, 365, 1964; Blumberg et al., JAMA 191, 541, 1965; Prince, Proc. Nat. Acad. Sci. USA, 60, 814, 1968] it became apparent that "serum hepatitis virus" was, in fact, contagious under certain circumstances. It therefore became appropriate to alter the terminology. The Committee on Viral Hepatitis of the Division of Medical Sciences, Academy of Sciences, National Research Council therefore recommended in 1972 a return to the former terminology, namely hepatitis A virus for infectious hepatitis virus and a hepatitis B virus for serum hepatitis virus. At the same time the committee recommended the use of the term hepatitis B antigen ($HB_sAg$) for the antigen in place of the previous term, e.g., Australia antigen (Au Ag), which had been employed inasmuch as the antigen had first been discovered in the blood of Australian aboriginies; Serum Hepatitis Antigen (SH); Hepatitis Associated Antigen (HAA); etc.

Subsequently, studies focused upon the antigenic specificites of hepatitis B virus infections and research centered about sub-type antigens now termed $HB_sAg$-/adywr, etc., the hepatitis B core antigen ($HB_cAg$) discovered by Almeida, the e-antigen(s) discovered by Magnius and Espmark as well as hepatitis B surface antigen ($HB_sAg$). Antibody to $HB_sAg$ is termed Anti-$HB_2$.

Many of the early researchers, including Blumberg, were of the belief that hepatitis B antigens were of host genetic origin. Other researchers, including Prince and Vnek, considered that hepatitis B antigens were determined by the genome of hepatitis B virus. It became increasingly evident that active immunization would be required to prevent infections by this virus, and to that end research focused upon the preparation of a vaccine.

Heretofore, particles in human sera having a particle size in the range of about 20 to 25 nm were regarded as the predominant particles which carry the hepatitis B surface antigens. Researchers focused about the separation of these particles from the other proteinaceous material in the blood, and especially from the larger 42 nm Dane particle which many suspected to be the infective virion. It was postulated that if the antigen could be purified to the required extent, and Dane particles removed, there could be provided a material which when diluted with a physiologically acceptable medium and further inactivated for safety, would provide a vaccine for active immunization. To this end Blumberg in U.S. Pat. No. 3,636,191 recommended the treatment of blood plasma from $HB_sAg$ carriers with a mixture of enzymes to digest new particle-associated proteins, followed by conventional centrifugation steps to recover purified hepatitis B surface antigen on particles having a particle size of about 22 nm. Blumberg et al. had recognized that the 22 nm hepatitis B surface antigen-associated particles were in the form of a shell which had no core and which was substantially resistant to the various enzymes employed in the digestion procedure. Blumberg provided a vaccine having a density of the order of 1.21 Gm/cc which, according to Blumberg, can be diluted with a physiologically acceptable medium and employed as an active immunizing agent.

The vaccine provided by Blumberg may be effective in inducing synthesis of antibodies in a host animal such as a human being, however, such antibodies are now known by us to be of limited specificity and do not include antibodies to the unique specificity(s), e.g., e-antigen, present only on the larger particles, such as the Dane particle (i.e., the virion). The vaccine proposed by Blumberg is thus not protective against the large doses of virus to which people are frequently exposed, e.g., in transfusions. (See FIGS. 1 and 2 which show the theoretical basis for this conclusion.) While it would theoretically be possible to produce very high titers of anti-HBs no acceptable means for doing this in man has been provided. Theoretically one could employ Freund's adjuvant to stimulate production of high quantities of antibodies. Then the very high concentrations of anti-HBs might effectively neutralize both hepatitis B surface antigen and the e-antigen-associated virions (see FIG. 2). However, because of potential carcinogenicity, and other adverse side effects of Freund's and other known adjuvants, no method is presently known for the production of such high titers of anti-HBs in man.

It has therefore become desirable to provide a vaccine against viral hepatitis which not only stimulates and induces the production of anti-HBs, but also that of antibodies specific to the virion itself, i.e., the 42 nm Dane particle, such as e-antigen(s). Production of such a vaccine has previously been impossible when pools of human $HB_sAg$-containing plasma are used as source material. The reason for this is that such plasma pools contain an excess of anti-e antibody. This combines with any e-antigen-containing particles, resulting in their precipitation. The precipitated e-antigen-containing particles are difficult if not impossible to purify by conventional methods, and therefore do not appear in the final product.

It is therefore an object of this invention to provide a means for isolating hepatitis B surface antigen together with free uncombined and unprecipitated e-antigen-containing particles to provide a vaccine for use in active immunization. It is a further object of this invention to provide a means for the multiplication of such antigens in a host animal, and followed by purification of the HB-associated antigenic material from the host animals blood to produce a broad and effective vaccine against viral hepatitis and related disorders.

SUMMARY OF THE INVENTION

In accordance with this invention there is provided a vaccine against viral hepatitis comprising:

A. Antigenic particles having a particle size in the range of 20 to 50 nm, said antigenic particles containing unprecipitated free uncombined hepatitis B surface antigens;

B. Said vaccine having less than 10 units of antibodies of hepatitis B surface antigen per 1,000 units of hepatitis B surface antigen;

C. At least 5% of the particles of said vaccine in the size range of 30 to 50 nm containing unprecipitated e-antigen(s), or similar Dane particle specific antigens. Such antigens are hereinafter loosely termed "e-antigen" as a conventional designation for what might more properly be called $HB_DAg$ (Hepatitis B Dane particle specific antigens);

D. Said hepatitis B antigen and said e-antigens being present in said vaccine in an amount sufficient to produce antibodies when introduced into a host animal, the balance being a medium which is physiologically acceptable.

Surprisingly, it has been found that a "select" few (Ca 2%) of clinically well people who carry hepatitis B surface antigen have particles containing free e-antigen. By this is meant that their blood not only contains $HB_sAg$ in a shell of particle size of about 22 nm (as reported by Blumberg and others) but also contains larger particles which are either filamentous particles with a diameter of 20 to 45 nm or Dane particles of generally cylindrical configuration having an average diameter of 42 nm which contain, in addition to conventional $HB_sAg$, e-antigen(s).

It has been found that vaccine can only be produced from the blood of these "select" (i.e., e-antigen positive, anti-e antibody negative) donors.

An important basis for this discovery is that the fact that Dane particles and the larger filamentous particles contain the e-antigen. This finding provides a rational basis for the associations summarized in Tables I and II.

Additionally, it has been found that e-antigen is also present in serum in a "soluble" form having a molecular weight of less than 1,000,000 generally 50,000 to 200,000, in addition to that present on the larger $HB_sAg$-associated particles. The blood of such e-antigen positive carriers of course, also contains the shell-like $HB_sAg$-associated particles of size of about 22 nm which lack e-antigen (see FIG. 1).

The rationale, as well as the theoretical advantage of this present vaccine, is illustrated by the schema shown in FIG. 2. Note that moderate titers of anti-$HB_s$ as would be provided by conventional 20 nm particle vaccines, such as Blumbergs, will provide protection only if the challenge dose is exceedingly low; when larger quantities of HB virus, and its associated $HB_sAg$-containing particles, are encountered, these will neutralize small quantites of anti-$HB_s$, leaving free and infective Dane particles able to infect the liver of the host. In marked contrast, when an anti-e response is induced this antibody(s) can specifically combine with the infective virions (Dane particles) without being neutralized by the vast excess (usually 500 small particles per 1 Dane particle) of small $HB_sAg$-associated particles.

The vaccine provided by the present invention is therefore characterized by the presence of particles in the range of 30 to 50 nm and preferably in the range of 35 to 45 nm. These larger particles, which are generally present together with particles of size of 16 to 22 nm, which also contain $HB_sAg$, are generally of two major types: i.e., filaments and Dane particles as described above.

The vaccine thus contains both antigenic specificities, proteins, and nucleis acids not present in the smaller $HB_sAg$-containing particles described in U.S. Pat. No. 3,636,191 (see FIG. 1). Note that Dane particles have a core as well as a shell, the core containing DNA, DNA polymerase and $HB_cAg$. The shell of the Dane particle contains $HB_sAg$ as well as e-antigen(s) and similar Dane-specific antigens. Therefore, the overall vaccine must contain particles having a higher density than the vaccine particles of U.S. Pat. No. 3,636,191. The density of the vaccine of the present invention is in the range of 1.23 to 1.34 preferably 1.24 to 1.34 as determined by isopycnic density gradient centrifugation in cesium chloride density gradients.

The vaccine is characterized as follows: each dose contains 20–50 μgm of $HB_sAg$ particle-associated protein containing $10^8$–$10^{12}$ Dane particles (preferably $10^{10}$–$10^{12}$); there are also additionally an equivalent or greater number of filamentous particles. It should be understood that the vaccine contains only those large (30–50 nm) particles in which the e-antigen is free, i.e., unassociated with the corresponding anti-e antibody.

The vaccine is especially characterized, therefore, by the presence of free e-antigen on Dane or filamentous particles. However, the vaccine can also contain e-antigen in a soluble form in the physiologically compatible medium which is employed.

The presence of the e-antigen can be detected by a number of methods; the following is adequate for the purposes of this invention:

INSENSITIVE TEST TO DETERMINE PRESENCE OF FREE E-ANTIGEN

The center well of an agar gel diffusion plate, preferably but not necessarily made with 0.5–0.7% agarose in 0.1 M NaCl, 0.01 M Tris buffer pH 7.2, 0.001 M EDTA containing 2.0 w/v Dextran 250, 0.1% w/v protamine sulfate, is filled with anti-e antiserum having specificity similar to that of the antiserum provided to us by Dr. Lars Magnius, and available from the Blood Derivatives Division of the New York Blood Center. Alternative peripheral wells are filled with either reference e-antigen (provided by Dr. Magnius), or similar to it by agar gel diffusion "identity test", or test serum. A precipitin line appearing within 3 days of incubation at room temperature, 30° or 37° C., which shows a reaction of identity with the reference antigen, indicates presence of large quantities of e-antigen. The characteristics of $HB_sAg$ carriers as a function of e-antigen and/or antibody is set forth in Tables 1 and 2.

TABLE 1

Characteristics of HBsAg Carriers As a Function of Presence of "e"-Antigen or Anti-"e" Antibody

| Characteristics | Results of Testing by Agar Gel Diffusion | |
|---|---|---|
| | "e"-Ag + | Anti-"e" + |
| Proportion of Blood Donor (asymptomatic HBsAg Carriers) | 1 – 5% | 30 – 70% |
| Proportion of HBsAg carriers on chronic renal dialysis units | 20 – 70% | 5 – 20% |
| Chronic Hepatitis found by Liver Biopsy | Most | Very Few |
| Chronic hepatitis suggested by elevated SGPT levels | Most | Very Few |
| Infective to contacts or offspring | Very | Probably not at all |

TABLE 2

Characteristics of HBsAg Carrier Plasma as a Function of Presence of "e"- Antigen or Anti-"e" Antibody

| Characteristics | Result of Testing by Agar Gel Diffusion | |
|---|---|---|
| | e-Ag + | Anti-e + |
| Dane particles in Plasma | $10^8 - 10^{12}$/ml | $<10^{6*}$ |
| HBsAg associated DNA polymerase in plasma | Detectable | Absent |
| HBcAg detectable in plasma by RIA or IAHA Tests | Detectable | Absent |
| HBsAg Titer | $10^{13} - 10^{14}$ particles/ml | $10^{12} - 10^{13}$ particles/ml |

*None seen by electron microscopy

METHOD OF PREPARING VACCINE

The method by which the vaccine is obtained is generally along the lines of patent application Ser. No. 426,825, now U.S. Pat. No. 3,951,937 the entire disclosure of which is hereby specifically incorporated herein. The critical phase is the first step, namely the use starting material composed of plasma obtained from chronic $HB_sAg$ carrier who have e-antigen(s) detectable by the above insensitive test. Such plasma of course also contains abundant Dane particles and filaments free of combined anti-e antibody (see above). Such plasma may be suitably obtained from clinically-well human chronic HB carriers, or alternatively from chimpanzees which have been naturally or artificially infected with HB virus, and have become chronic e-antigen positive $HB_sAg$ carriers. Generally speaking, plasma will be employed which contains $HB_sAg$ of the desired sub-type or sub-types. The starting plasma must contain e-antigen detectable by the insensitive methods set forth above and must contain no detectable anti-e antibody detectable by the above method. Such plasmas are relatively rare but are essential to the process.

Given starting material of the desired characteristics, as described above, a simple method for the isolation of the e-antigen-containing larger particle fractions, together with some contaminating smaller $HB_sAg$-containing particles, and with only minor contamination of serum proteins is provided by the following process:

1. Differential precipitation of antigen with polyethylene glycol; and
2. Absorption of contaminants by hydroxylapatite under conditions which prevent adsorption of the larger $HB_sAg$-containing particles, e.g. 24 to 50 nm.

The resulting product can be readily concentrated, stabilized with small quantities of human serum albumin, suspended in a physiologic vehicle and rendered non-infectious by combination of viral inactivation techniques well known to the art of vaccine production. Immunogenic quantities are then injected at intervals sufficient to provide an adequate and long-lasting anti-e as well as anti-$HB_s$ response. Such immunization is expected to provide protection against both high and low dose infections with hepatitis B virus. Protection against such low high dose infections by the known hepatitis B vaccine is difficult, it not impossible.

DETAILED DESCRIPTION OF INVENTION

Source Material

Plasma used as source material for the purification procedures detailed below is obtained by conventional plasmaphoresis procedures from chronic $HB_sAg$ carriers. These may be humans or animal species such as chimpanzees in which the chronic HB carrier state can be induced. The chimpanzee offers the practical advantage that it can be infected with human hepatitis B strains of any desired immunologic sub-type, and can develop chronic carrier state infections which in our experience show particularly high titers of $HB_sAg$ and are frequently associated with high concentrations of both Dane particles and e-antigen. Furthermore, these animals can be conveniently plasmaphoresed at frequent intervals without damage to their health or reduction in $HB_sAg$ or e Ag content of their plasma.

The plasma pool selected for use as a starting material for this vaccine must have:

A. e Ag detectable by an insensitive method such as agar gel diffusion. It should be noted that only 1–5% of chronic $HB_sAg$ carriers found among blood donor populations satisfy this criterion.

B. No detectable anti-e antibody. It should be noted that the majority of $HB_sAg$ carriers found among blood donor populations have anti-e antibody. If such plasma were pooled with the desired plasma it would result in precipitation of the e-antigen-containing particles, and would prevent their isolation by the methodology described.

C. Dane particles readily detectable by conventional techniques of electron microscopy (negative staining) preferably in large concentrations.

D. Sub-type antigenic composition of $HB_sAg$ which includes the major sub-types encountered in the geographic region for which vaccine is designed. For example, a vaccine to be used in southeast Asia should preferably contain a predominance of the r sub-type, whereas a vaccine designated for use in Europe or the United States should preferably contain $HB_sAg$ predominantly of the w sub-type.

E. Plasma from a sufficient number of doors, representing a mixture of the sub-types prevalent in the geographic area for which the vaccine is designated, to provide broad immunologic coverage. In most cases a minimum of 10 donors would be desirable. The use of "hybrid strains" such as $HB_sAg$/adywr offers obvious advantages. Such hybrid strains can be propagated in the chimpanzee.

F. The starting material should be frozen at $-70°$ C. within 4 hours of collection and should be held at $4°$ C. during the interval prior to freezing.

G. Starting material should be bacteriologically sterile and should be free of adventitious viruses detectable by conventional techniques of virus isolation (inoculation of embryonated eggs, tissue cultures, suckling mice, guinea pigs and rabbits), as currently practiced in the quality control of other viral vaccines.

As indicated above, the purification can be conducted in the manner of Ser. No. 426,825, mentioned, supra. In such instance the fluid blood material-containing antigen is purified to remove impurities from the antigen-containing material by initially maintaining the pH of the blood material within the approximate range of 4.4 to 4.7. This results in a small amount of precipitate which, together with remaining cells and cell debris can be removed by moderate speed centrifugation, e.g., 20 minutes at 10,000 rpm. Thereafter, the material is admixed with 2.5 to 4.5 weight percent of polyethylene glycol, preferably 3.0 to 4.5. The lower concentrations, say 3–4%, can selectively precipitate large particle forms and therefore, are advantageous under certain circumstances. The pH is maintained at 4.4 to 4.7. The weight percent of the polyethylene glycol is based upon the total weight of the mixture. This precipitates hepatitis B-containing antigen material of the large particle size, e.g., 30 to 50 nm, as well as a proportion of the known shell-like hepatitis B surface antigen-containing material. The precipitate is recovered, and an amount of water is added such as to present an intermediate fluid material having an antigen concentration the same or higher as in the original blood material. The pH of the intermediate fluid material is adjusted in the range of about 4.9 to 5.1, optimally 5.0, whereby there is formed a precipitate containing proteinaceous material and polyethylene glycol and a fluid phase containing type B hepatitis antigen further characterized by the presence of Dane particles and/or filamentous material. The fluid phase is separately recovered, and the pH is adjusted to be in the range of approximately 4.4 to 4.7. The fluid phase is thereafter admixed, while it is maintained in this pH range, with 3.0 to 4.5 weight polyethylene glycol, based on the total weight of the mixture, to produce a precipitate containing:

A. Purified hepatitis B surface antigen containing particles of shell-like configuration of particle size between 20 and 30 nm; and B. (1) Filamentous particles containing $HB_sAg$ and e-antigen which is free of any anti-e antibody, said filamentous particles being of a diameter between 20 and 50 nm, and (2) Dane particles of generally spherical configuration, being of a particle size of 40 to 50 nm, and having a lipoprotein outer shell containing $HB_sAg$ and e-antigens and containing a core, containing DNA, DNA polymerases and $HB_cAg$.

The purified antigenic material is recovered. Thereafter, it can be treated to inactivate the virus, whereby the material is in a form for dilution with a physiologically acceptable medium.

Preferably, in such a separation the temperature of each of the mixtures after each of the mixing steps is maintained in the range of 0° to 8° C. during the production of the precipitates. The purification step is facilitated if recovery is augmented by the use of centrifugation following the precipitation steps. Polyethylene glycol which is employed can be used as such, or in the form of an aqueous solution, preferably one which is about 30% by weight polyethylene glycol. Generally, this polyethylene glycol is one which has a molecular weight in the range of 500 to 50,000, preferably about 6,000.

Further purification can be effected by subjecting the purified antigens to adsorption on hydroxylapatite utilizing batch or column chromatographic procedures. In the latter instance, the partially purified antigens are passed through a chromatographic column containing hydroxylapatite to which they adsorb. Further purified antigens are then recovered using a multi-, e.g., about 3-step, elution procedure. Particles of particle size 25 to 50 nm are recovered separately from a fraction of particles of smaller size (16–22 nm) and from the bulk of serum proteins.

INACTIVATION OF INFECTIVITY

Following purification, the large particle fraction can be anticipated to be infectious. It is, therefore, necessary that chemical and physical procedures be employed to effectively inactivate any and all infectivity. Hepatitis virus is known to be very stable. This probably results in part from the small size of its nucleic acid, as well as other properties of its tertiary and quaternary structure and morphologic organization.

Inactivation can be carried out by any combination of the various conventional techniques known to the art of vaccine manufacture. The use of combinations is expected to eliminate "resistant fractions" which may be expected with any single inactivation technique. These are destroyed by a second or third technique having a different principle of inactivation from that formerly applied. This is the conventional approach for avoiding resistant fractions, e.g., in the treatment of certain bacterial infections, where drug resistant variants are common, by the use of combination antibiotic therapy. A schematic representation of this principle is illustrated in FIG. 3.

Any combination of presently well known techniques of inactivation which satisfy this criterion can be employed. The following, preferably in combination, is suggested:

1. Irradiation from a cobalt source with 2,500,000 rads;

2. Treatment with formalin at a concentration of 1:2,000 for 4 days at 37° C. using conventional techniques. The vaccine is clarified by filtration through a Millipore 0.22μ filter, or equivalent, to remove any aggregates prior to the addition of formalin or β-propriolactone;

3. Use of β-propriolactone under conditions currently used for inactivation of rabies vaccine.

After inactivation the final product is diafiltered with an Amicon PM30 filter, or equivalent, against 0.9% NaCl, containing 1:10,000 Thiomerosal, and any desired conventional stabilizer, to remove any low molecular weight compounds used for or resulting from the inactivation procedures, and is then sterile filtered and aseptically dispensed into sterile vials for lyophilization, or freezing, as preferred. Thiomerosal is sodium ethyl mercurithiosalicylate, a conventional antibacterial preservative. The Amicon PM30 filter is a cellulose filter having an average pore diameter which nominally excludes molecules having a molecular weight of greater than 30,000.

SAFETY TESTING

Thereafter, the batch is tested to determine that it is safe, i.e., free of infectivity. Until such time as there is a tissue culture technique or other standard test to determine the safety of HB and related virus infectivity, it is necessary that each batch of vaccine made for human use be tested by inoculation of HB seronegative susceptible animals, such as chimpanzees or gibbons. At least four seronegative animals (two inoculated with 5×20 μgm doses and two inoculated with 500×20 μgm, i.v.) should be used for this purpose. A satisfactory batch will not result in either hepatitis, $HB_sAg$ production, or an anti-HBc response, each detected by the most sensitive methods currently available, in any inoculated animal. The safety, i.e., lack of infectivity, can readily be determined by such a technique. Of course larger numbers of animals will be used for evaluation of the early batches prior to clinical trials.

POTENCY TESTING

Vaccine is adjusted to a concentration of generally about 5 to 100 μgm, preferably 20 to 50 μgm of $HB_sAg$-associated protein per dose, to give suitable immogenicity. Generally speaking, the quantity of e-antigen-containing particles in such dose will amount to about 2 to 5 μgm. Potency is controlled by determining the minimal concentration of each batch of vaccine which gives a definite specific anti-$HB_s$ and anti-e response in guinea pigs, mice, or other suitable test animals.

Finally, the vaccine must have sufficient potency to provide an anti-$HB_s$ titer of at least 1:100 by passive hemagglutination (standardized by tests on a frozen anti-serum control) in at least four chimpanzees immunized with two doses of the standard vaccine in accordance with the recommended schedule; and furthermore, anti-$HB_s$ must remain detectable at a titer of greater than 1:10 for at least one year following the onset of immunization of these chimpanzees. In addition, the chimpanzees must respond with a measurable anti-e response.

DOSAGE ADMINISTRATION AND UTILIZATION

Vaccine can be administered by sub-cutaneous or intramuscular injection. While the preferred route has not been yet determined, it is believed that intramuscular injection is preferred. The frequency of administration is usually about two doses one month apart, followed by a booster at six months to one year after primary immunization. Of course, the dosage will depend upon the size of the host animal being inoculated. The subsequent doses or the booster will depend upon the level of antibody in the blood as a result of the initial immunization. Licensable adjuvants conventionally employed in vaccine manufacture can be utilized.

The vaccine is recommended for all persons at risk of developing hepatitis B infection, and particularly those at especially high risk, such as patients and staff on hemodialysis units, medical personnel, persons of tropical populations and those visiting the tropics. In the case of tropical populations, particularly in Africa, Asia, the mediterranean region and South America, where a high incidence of hepatitis B infections has been consistently observed, the vaccine should be administered sufficiently early in life to prevent acquisition of chronic carrier state infections which tend to occur in these regions during the first five years of life.

When adequate supplies are available, and effectiveness has been documented, the vaccine will be useful for all persons not already protected against hepatitis B infections as a result of prior immunity.

The particular importance of hepatitis B vaccine lies in its role in prevention of the chronic hepatitis B carrier state with its attendant risk of development of chronic liver diseases, such as chronic active hepatitis, cirrhosis and hepatoma. The association of a chronic hepatitis B carrier state and these diseases is now abundantly documented, and the role of chronic hepatitis B as a cofactor in the etiology of these conditions is also established [Prince, A. M., in *The Liver: Normal and Abnormal Functions*, edited by F. F. Becker (M. Dekker, New York) 1975].

The use of the new hepatitis B-containing vaccine in the long run can have a significant effect in the prevention of these chronic liver diseases which are so extraordinarily prevalent in those regions, primarily in the tropics, where chronic hepatitis B carrier state is unusually frequent. For example, in Senegal where 14% of the population chronically carry $HB_sAg$, the attack rate of primary liver cancer is 50 to 100 times as high as that observed in the United States, where only an average of approximately 0.3% of the population are chronic carriers of hepatitis B virus.

It should be emphasized that the approaches to purification of the large particle fractions described in the present invention are not the only approaches available for this purpose. Variations designed to meet individual needs and preferences can be employed, and these include those known or to be hereafter developed. What is important and what is contemplated by the scope of the invention is the use of large particle, e-antigen-containing fractions which have routinely been discarded by prior art researchers. Thus, all vaccine containing such particles; or specific soluble components of such particles; or synthetic antigenically specific sub-units thereof, are contemplated as these are useful in an active immunization program against e-antigen or similar Dane particle specific antigens.

BRIEF DESCRIPTION OF DRAWINGS

Referring to the drawings herein,

FIG. 8 shows the results of immunoelectrophoresis of fractions of HBsAg/e which has been eluted from hydroxylapatite, the immunoelectrophoresis being conducted in agrose gel. The samples were tested with antiserum prepared by immunization of rabbits with normal chimpanzee plasma.
  Samples: (1) Pool I; (2) Pool II; (3) Pool III; (4) Pool IV; (5) Pool V; (6) Pool VI; (7) Pool VII--VIII;

FIG. 10 shows the result of polyacrylamide gel electrophoresis of samples of purified HBsAg/e run parallel with those in FIG. 9. The gels after Schiff base staining were scanned in a Joyce-Loebl microdensitomer;

FIG. 11 is a series of electron microscopes of HBsAg/e particles which have been purified by batchwise elution from hydroxylapatite and rate zonal centrifugation. Pictures were taken after negative staining with phosphotungstate in a JEOL 100B cleatron microscope at 67,000 magnification.
  a: Rate zonal centrifugation - Pool I: Dane particles and large filaments.
  b: Rate zonal centrifugation - Pool II: filaments 22–28 nm spherical particles.
  c: Rate zonal centrifugation - Pool III: 20–28 nm spherical particles;

FIGS. 12A and 12B are graphic representations of data revealed by thin-layer isoelectric focusing of pooled concentrated samples of HBsAg/e in Sephadex G-75 suspended in 1% pH 3–6 ampholine. The fractions were analyzed for HBsAg by RIA (•—•—•) and for pH (x—x—x) as described above.
  A: Pool I: 22–28 nm spherical particles of HbsAg.
  B: Pool II: 22–28 nm spherical particles, filaments and a few Dane particles; and FIG. 13 show additional data obtained from thin-layer isoelectric focusing of the same material with 1% pH 3.5–10.0 ampholine of pooled concentrated samples of HBsAg/e (Table 4) after Triton X-100 treatment. The fractions were analyzed for HBsAg by RIA (•—•—•) and for pH (x—x—x) as described above.
  A: Pool I: 22–28 nm spherical paeticles.
  B: Pool II: 22–28 nm spherical particles, filaments and a few Dane particles.

EXAMPLES

Figure 1:
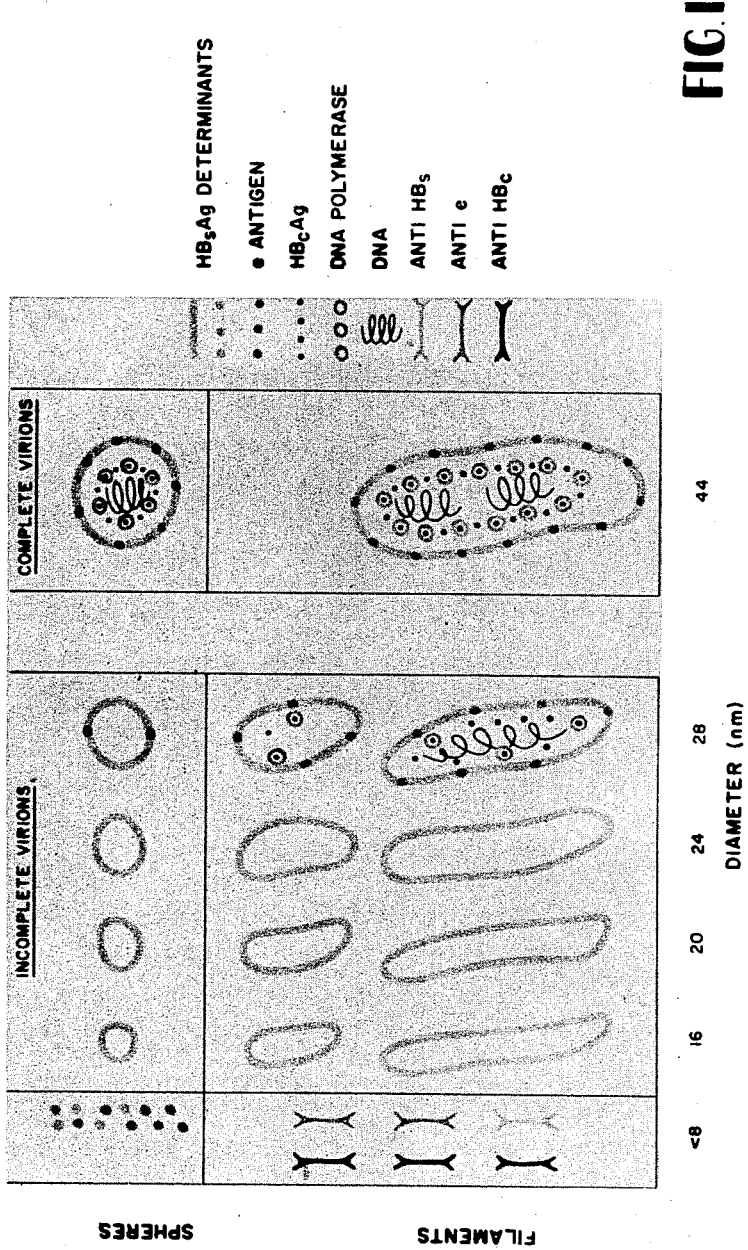
FIG. 1 shows in a graphic fashion the diverse morphologic forms associated with hepatitis B surface antigen, it being understood that together with the hepatitis B surface antigen in accordance with the present invention there is e-antigen which can be present on Dane particles which contain hepatitis B core antigen (HBcAg), these Dane particles being characterized by deoxyribonucleic (DNA) and its polymerase. The figure shows the possible antibodies including antibodies of hepatitis B surface antigen, antibodies of hepatitis B core antigen and antibodies of e-antigen.

In order to more fully illustrate the nature of the invention and the manner of practicing the same, the following examples are presented.

Above there are outlined the general steps for purification of hepatitis B surface antigen from human or chimpanzee plasma by polyethylene glycol precipitation (PEG) followed by purification on hydroxylapatite. Set forth below are the results of the application of these procedures for large scale purification and fractionation of chimpanzee hepatitis B surface antigen containing particles having e-antigen. The samples at individual steps of purification were analyzed in detail using electrophoretic and chromatographic techniques. Comparative studies were performed with fractions of different morphological forms of purified chimpanzee HBsAg associated particles by thin-layer isoelectric focusing and polyacrylamide gel electrophoresis.

EXAMPLE 1: PURIFICATION AND CHARACTERIZATION OF HB ASSOCIATED PARTICLES FROM 7.8 LITERS OF PLASMA FROM A SINGLE HBsAg CARRIER CHIMPANZEE.

Materials and Methods

Source of HBsAg

The antigen was purified from pooled plasma of a carrier chimpanzee previously inoculated with human HBsAg-positive plasma of the adw subtype. The e-antigen was present on the surface of identifiable Dane particles in the plasma used.

Purification of HBsAg and e-Antigen

HBsAg and e-antigen was isolated from plasma by polyethylene glycol (PEG) precipitation. The resuspended precipitate of HBsAg and e-antigen was purified by column chromatography on hydroxylapatite. The final steps of purification involved density gradient centrifugation. The methods of purification were essentially the same as outlined in Ser. No. 426825, hereby incorporated by reference. The procedures are briefly described as follows:

Precipitation of HBsAg and e-Antigen by PEG:

In a pre-purification step, 7,800 ml of HBsAg and free e-containing plasma was adjusted to pH 4.6 and a 30% solution of PEG in distilled water was added to approximately 2% concentration. The solution was stored overnight at 4° C. and clarified by centrifugation. The HBsAg in the supernatant was precipitated by raising the PEG concentration to 4%. The supernatant after overnight storage of the sample at 4° C. was decanted and discarded. The sediment of HBsAg (containing e-antigen) was resuspended to 500 ml in distilled water. The bulk of PEG with some accompanying contaminants was precipitated by adjusting the solution to pH 5.0 and the precipitate was removed by centrifugation. The clear supernatant was readjusted to pH 4.6, and the HBsAg and particle associated e-Ag (HBsAg/e) was precipitated by adding a 30% solution of PEG to a final concentration of 4%. The HBsAg/e was removed by centrifugation after overnight storage of the sample at 4° C. Finally, the precipitate of HBsAg/e was resuspended to 320 ml in distilled water.

Column Chromatography on Hydroxylapatite:

In a trial experiment, 50 ml of resuspended PEG precipitate of HBsAg/e was applied to a 6.5 × 16.5 cm. column of hydroxylapatite and eluted with a discontinuous gradient of phosphate buffer. In a subsequent experiment 200 ml of the sample was partially purified on a 6.5 × 35 cm column of hydroxylapatite. The HBsAg eluted with the first protein peak was passed through a hydroxylapatite column for a second time.

Density Gradient Centrifugation

Fractions of HBsAg isolated by column chromatography were purified by rate zonal centrifugation. A discontinuous gradient was formed using 3 ml of 60% and 7 ml of 40% sucrose in 0.02 M sodium phosphate buffer pH 7.2 (containing 0.02% $NaN_3$). A 20 ml volume of sample was applied to each tube and centrifuged in a Spinco SW 25.1 rotor at 18,000 rpm for 18 hours. Fractions of 1 ml volume were collected by dripping from the bottom of tubes and analyzed for HBsAg. The peak fractions of antigenic activity were pooled, thoroughly dialyzed and concentrated by ultrafiltration using a membrane with a 30,000 MW cutoff (Amicon PM-30). The concentrated fractions of HBsAg were submitted to final steps of purification by isopycnic banding in a linear CsCl gradient and rate zonal centrifugation in a continuous sucrose gradient under conditions normally employed.

Detection Methods

HBsAg was monitored by counter electrophoresis (CEP) or solid phase radioimmunoassay (Ausria I or II, Abbott Laboratories). The protein concentration was estimated by measurements of O.D. at 280 nm and by micro Kjehldahl technique. The methods used were the same as previously described in the above-identified patent application.

Criteria of HBsAg Purity

The samples after each step of purification were analyzed by cellulose acetate electrophoresis, immunoelectrophoresis, and agar gel diffusion tests against polyvalent anti-normal human plasma protein antiserum.

Polyacrylamide Gel Electrophoresis

Aliquots of samples containing 0.01 sodium phosphate buffer pH 7.2, 1% sodium dodecylsulfate, 1% $\beta$-mercaptoethanol and 10% glycerol were heated for two minutes in a boiling water bath, applied to 7.5% or 10% sodium dodecylsulfate-acrylamide gels, and elto Maizel. The gel was stained for proteins by Coomassie Blue staining and for carbohydrates by Schiff base staining according to the method of Glossman and Neville.

RESULTS

The results of purification of HBsAg/e positive sera by polyethylene glycol precipitations are presented in Table 3. Apparently about 87% of the original plasma protein was removed in the first step of precipitation of HBsAg (which included pre-purification at 2% PEG concentration). The final preparation after two successive PEG precipitation steps showed quantitative recovery of HBsAg with only 4% of the original proteins.

TABLE 3

PURIFICATION OF POOLED CHIMPANZEE HBsAg BY PEG 6000 PRECIPITATION

| SAMPLE | VOLUME (ml) | HBsAg CEP TITER[1] | TOTAL PROTEIN (g) | % YIELD[2] HBsAg | FOLD[3] PURIFICATION |
|---|---|---|---|---|---|
| Original HBsAg-Plasma | 7,800 | 512 | 429.0 | 100 | — |
| First 4% PEG Precipitate | 500 | 7,080 | 55.0 | 89 | 6.9 |
| Second 4% PEG Precipitate | 320 | 10,000 | 16.6 | 80 | 20.7 |

[1]Kjehldahl

[2] $\frac{[HBsAg] \text{ Sample} \times \text{Volume}}{[HBsAg] \text{ plasma} \times \text{volume}} \times 100$

Figure 4:
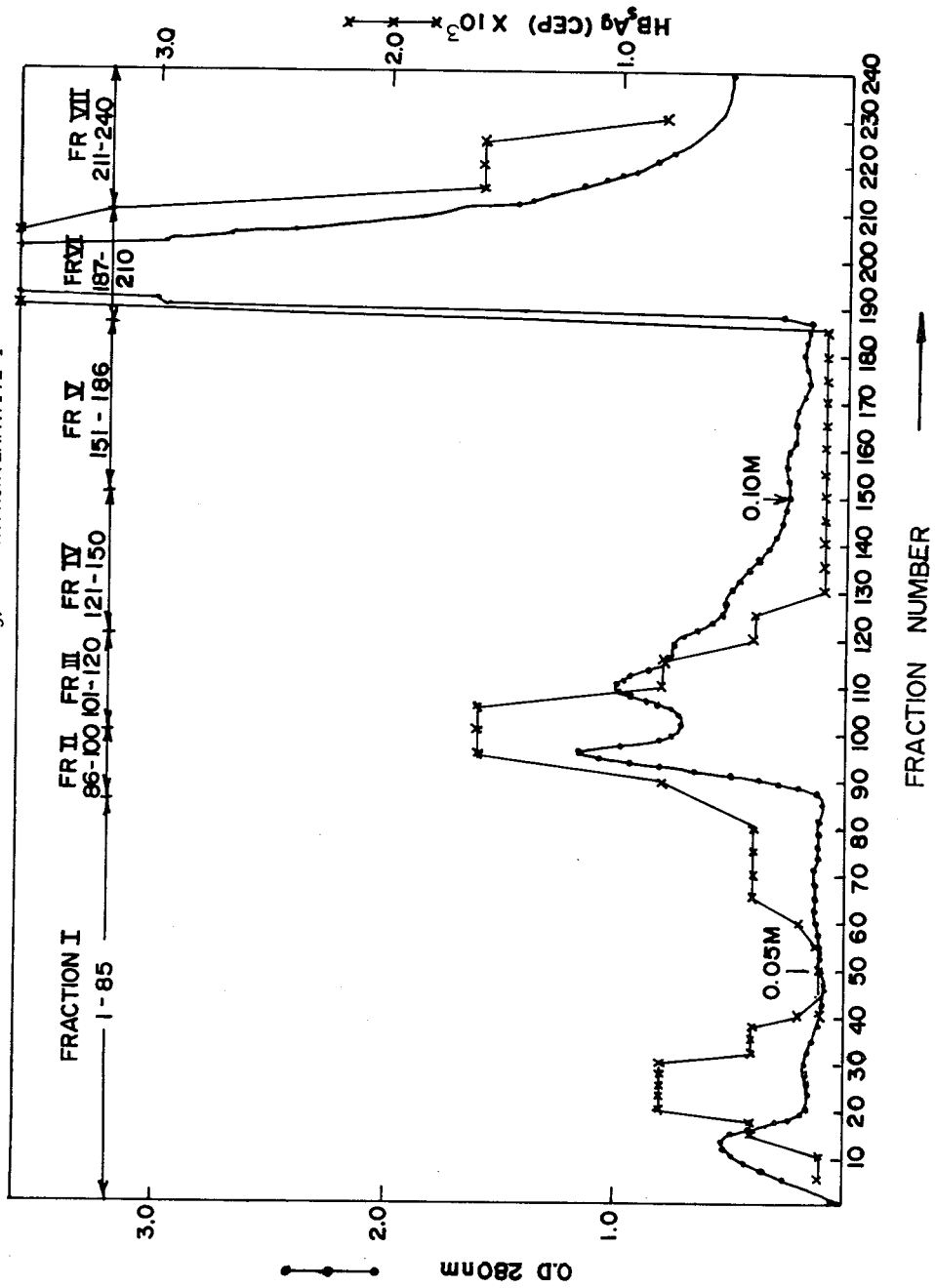
FIG. 4 is a figure reflecting the chromatographic results obtained by the column chromatographic fractionation of a PEG precipitated HBsAg material on a 500 ml column of hydroxylapatite. The data was derived by resuspending PEG precipitated HBsAg/e in 50 ml volume of liquid and it was chromatographed on a 500 ml column of hydroxylapatite. The antigen was eluted with a discontinuous gradient of 1 liter each of 0.02 M, 0.05 M and 0.10 M sodium phosphate buffer pH 7.2. Fractions of 10 ml volume were collected and alalyzed for protein by O.D. at 280 nm (•—•—•) and for HBsAg by CEP (x—x—x)

[3] $\frac{[Protein] \text{ Plasma}}{[Protein] \text{ Sample}} \times \frac{\% \text{ Yield HBsAg}}{100}$ Hydroxylapatite Chromatography I In a preliminary experiment, a 50 ml volume of resuspended PEG precipitate of HBsAg was fractionated by column chromatography on hydroxylapatite. The results of chromatography are illustrated in FIG. 4. The eluate was pooled into seven fractions, which were dialyzed against 0.02 M sodium phosphate buffer of pH 7.2 (containing 0.02% sodium azide) and concentrated by ultrafiltration. The concentrated samples were analyzed for proteins by O.D. measurements at 280 nm and for HBsAg by CEP. The results of fractionation are summarized in Table 4.

TABLE 4
HYDROXYLAPATITE CHROMATOGRAPHY I
PURIFICATION OF THE SECOND 4% PEG PRECIPITATE OF HBsAg

| NO. | SAMPLE | | VOLUME (ml) | HBsAg CEP TITER | TOTAL[1] PROTEIN (mg) | % YIELD[2] HBsAg | FOLD[3] PURIFICATION |
|---|---|---|---|---|---|---|---|
| 1 | Second 4% PEG precipitate HBsAg | | 50 | 10,000 | 2,600.0 | 100 | 0 |
| 2 | Ottapatite I: | Pool I | 4 | 10,000 | 63.2 | B | 3.3. |
| 3 | | Pool II | 6 | 10,000 | 87.2 | 12 | 3.6 |
| 4 | | Pool III | 5 | 10,000 | 183.9 | 10 | 1.4 |
| 5 | | Pool IV | 6 | 800 | 110.0 | 1 | 0.2 |
| 6 | | Pool V | 6 | 800 | 72.6 | 1 | 0.3 |
| 7 | | Pool VI | 10 | 20,000 | 984.0 | 40 | 1.1 |
| 8 | | Pool VII | 7 | 10,000 | 338.3 | 14 | 1.1 |

[1] #1 Kjehldahl #s 2-8 O.D. 280 nm $E_{1cm}^{0.1\%} = 1.143$

[2] $\frac{[HBsAg]\ sample \times volume}{[HBsAg]\ plasma \times volume} \times 100$

Figure 5:
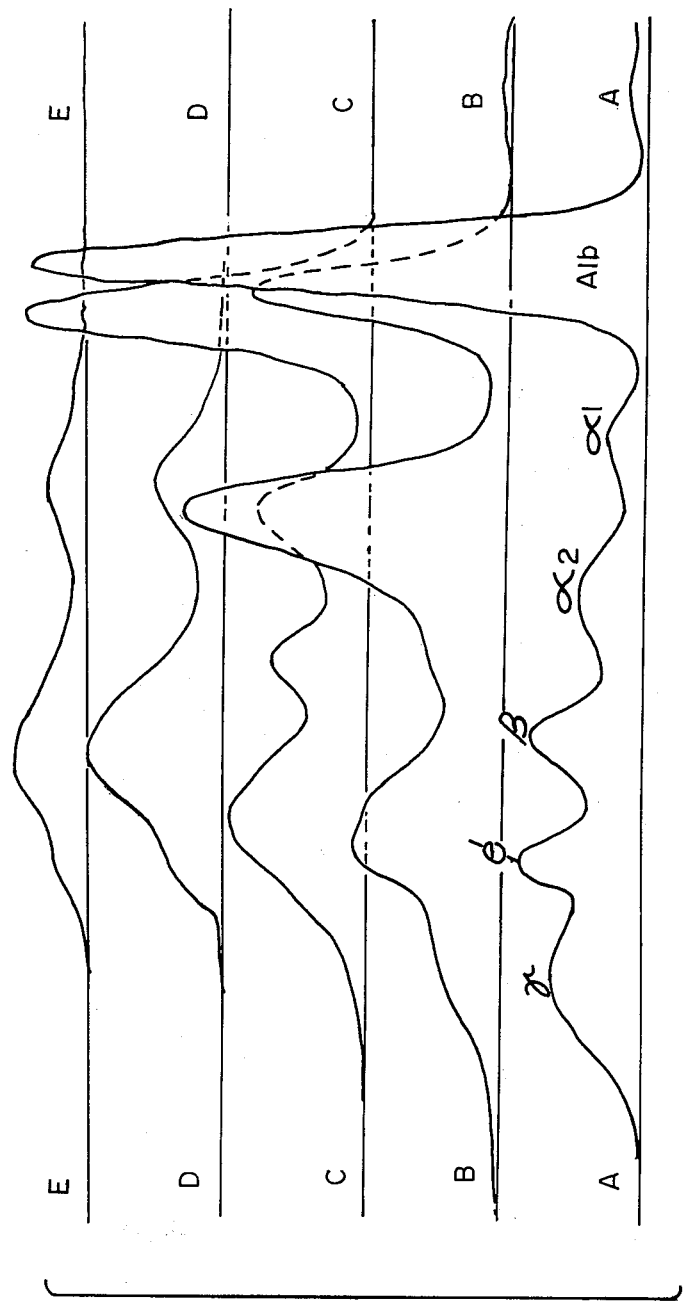
FIG. 5 depicts the results of cellulose acetate electrophoresis of pooled concentrated samples of HBsAg/e which has been purified by chromatography on hydroxylapatite (Table 4). The strip was scanned in a Beckman microzone densitometer after Ponceau red staining.
  Line A: the original HBsAg/e containing plasma.
  Line B: the resuspended PEG precipitate of HBsAg/e.
  Line C: column eluate of HBsAg/e - Pool III.
  Line D: column eluate of HBsAg/e - Pool II.
  Line E: column eluate of HBsAg/e - Pool I.

[3] $\frac{[Protein]\ Plasma}{[Protein]\ Sample} \times \frac{\%\ Yield\ HBsAg}{100}$ Cellulose acetate electrophoresis (FIG. 5) showed in comparison to the original plasma (FIG. 5A) two protein bands in Fraction I (FIG. 5E) and Fraction II (FIG. 5D) migrating between alpha$_1$, alpha$_2$ and between fibrinogen and beta globulin regions. Fraction III (FIG. 5C) showed two additional components in the beta globulin and albumin regions. The suspended PEG precipitate of HBsAg (at 24 × fold concentration) showed strong lines between alpha$_1$ and alpha$_2$ region and in the origin (fibrinogen) and two additional bands in the albumin and gamma globulin regions (FIG. 5 B).

As indicated in FIG. 4, HBsAg was separated into three peaks of antigenic activity. The samples analyzed by electron microscopy showed mostly spherical particles of 22 to 28 nm in diameter in the first peak (Fraction I); variable size particles, including Dane particles and large filaments, in the second peak (fraction II). The third peak of antigenic activity (Fraction VI) contained mostly 16 to 22 nm spherical particles.

Hydroxylapatite Chromatography II

Figure 6:
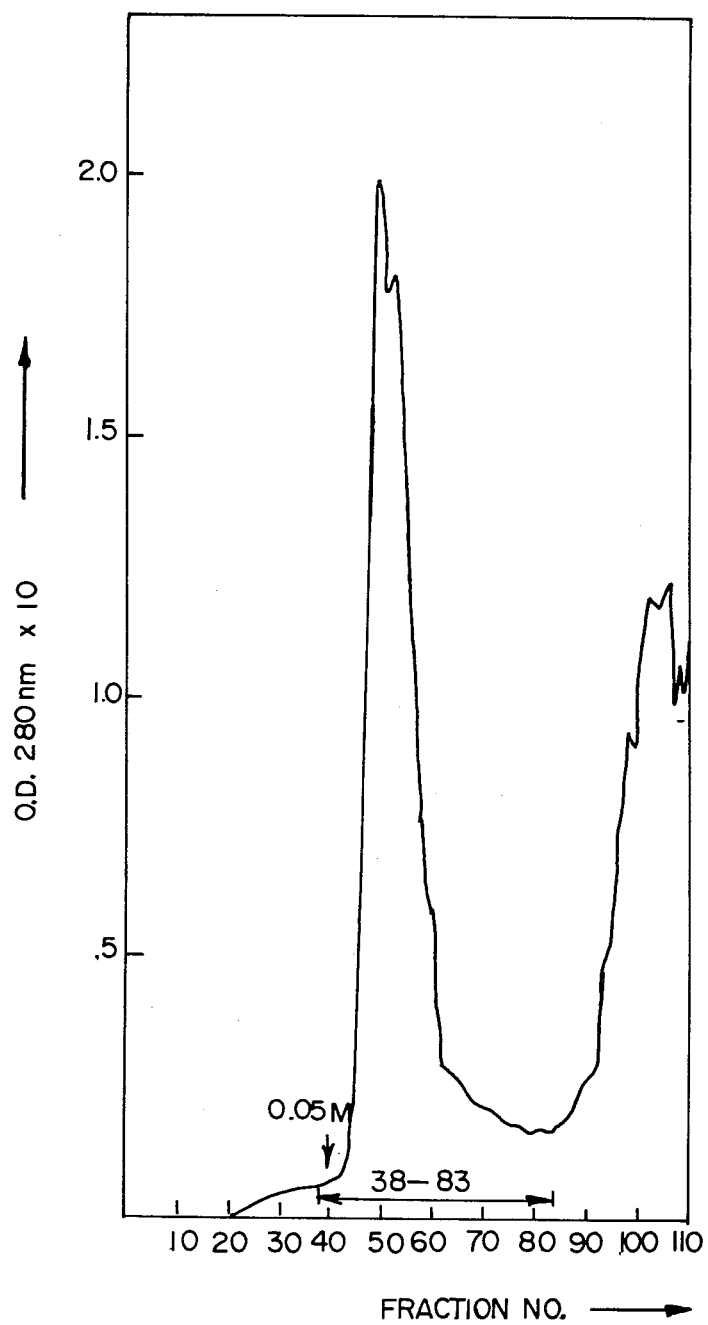
FIG. 6 is a graphic drawing showing the results of the purification of a PEG precipitated HBsAg/e material by column chromatography on hydroxylapatite. A 200 ml volume of resuspended PEG precipitate of HBsAg/e was applied on a 1000 ml volume column of hydroxylapatite. The antigen was eluted with a discontinuous gradient of 0.5 liters of 0.02 M and 1 liter of 0.05 M sodium phosphate buffer pH 7.2. Fractions of 12 to 13 ml were collected and analyzed for proteins by O.D.

A further 200 ml volume of the resuspended PEG precipitate of HBsAg was fractionated on a 1000 ml volume column of hydroxylapatite. The results of chromatography are illustrated in FIG. 6. The fractions of HBsAg from the first protein peak (pool I: fractions 38 to 83) and the residual eluate (pool II: fractions 84–110) were each pooled and concentrated to 75 ml by ultrafiltration.

Hydroxylapatite Chromatography III

Figure 7:
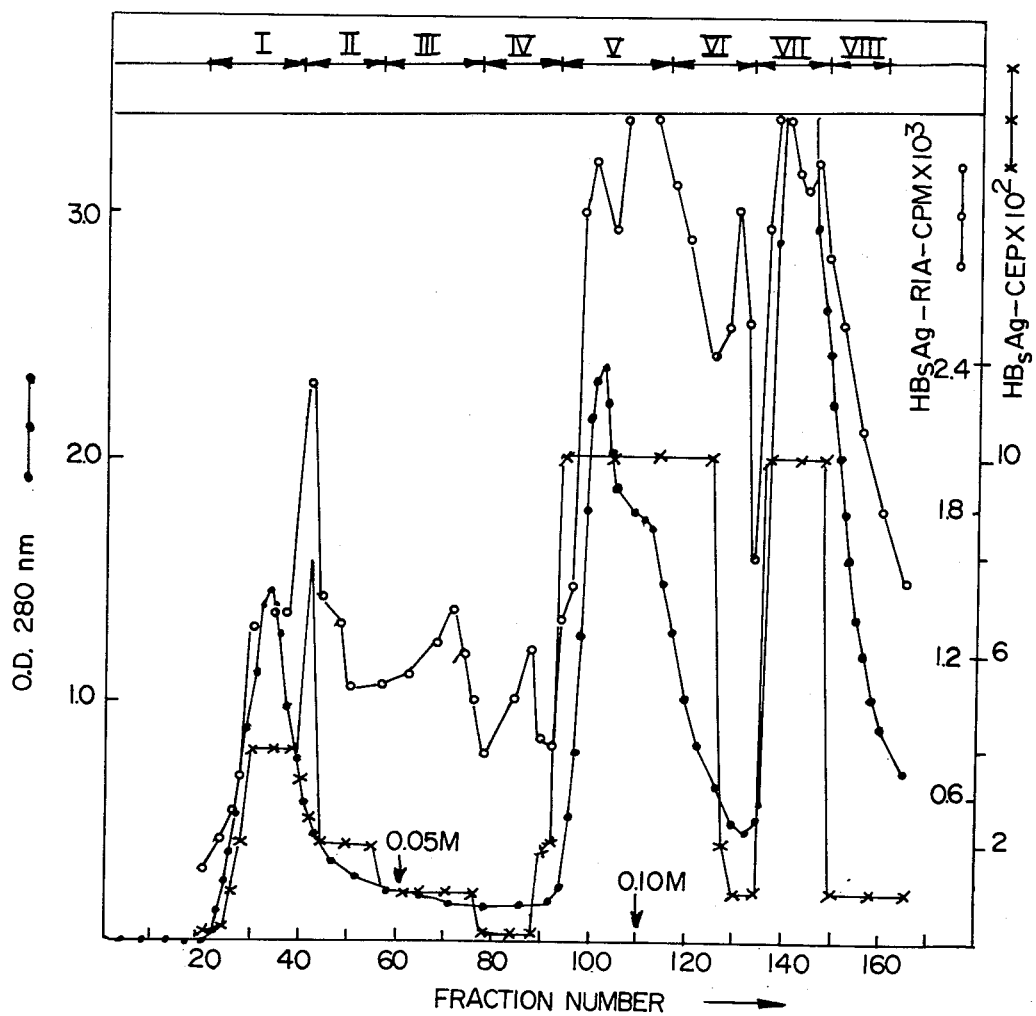
FIG. 7 is a graphic drawing showing the results of column chromatography performed on a HBsAg/e material on hydroxylapatite. Pool I of HBsAg/e eluted from hydroxylapatite II (FIG. 6) was concentrated to 75 ml and reapplied on a 600 ml column of hydroxylapatite. The antigen was eluted with a discontinuous gradient of 1 liter each of 0.02 M, 0.05 M and 0.10 M sodium phosphate buffer pH 7.2. Fractions of 18 ml volume were collected and analyzed for proteins by O.D. at 280 nm (•—•—•), for HBsAg by CEP (x—x—x) and RIA (o—o—o)

The concentrated sample from pool I of the above separation was rechromatographed on a 1000 ml volume column of hydroxylapatite. The results of this chromatography are illustrated in FIG. 7. The eluate was pooled into eight fractions according to the figure. The pooled samples were concentrated by ultrafiltration and washed with 0.02M sodium phosphate buffer pH 7.2 (containing 0.02% sodium azide as described above.) The samples were analyzed for proteins and HBsAg and the results are summarized in Table 5.

TABLE 5
HYDROXYLAPATITE CHROMATOGRAPHY III
PURIFICATION OF POOL FROM HYDROXYLAPATITE CHROMATOGRAPHY II

| SAMPLE | | VOLUME (ml) | HBsAg CEP Titer | TOTAL[1] PROTEIN (mg) | % YIELD[2] HBsAg | FOLD[3] PURIFICATION |
|---|---|---|---|---|---|---|
| O Hydroxylapatite II: | Pool I | 75 | 10,000 | 706.0 | 100 | — |
| O Hydryxylapatite III: | Pool I | 5 | 8,000 | 51.8 | 5.3 | 0.12 |
| | Pool II | 5 | 2,000 | 14.2 | 1.3 | 0.65 |
| | Pool III | 4 | 1,600 | 11.4 | 0.9 | 0.56 |
| | Pool IV | 4 | 3,200 | 7.3 | 1.7 | 1.64 |
| | Pool V | 12 | 16,000 | 181.6 | 25.6 | 1.00 |
| | Pool VI | 7 | 8,000 | 79.6 | 7.5 | 0.61 |
| | Pool VII | 45 | 4,000 | 332.8 | 24.0 | 0.51 |

[1] $O.D._{280}\ nm\ E_{1cm}^{0.1\%} = 3.16$

[2] $\frac{[HBsAg]\ sample \times volume}{[HBsAg]\ plasma \times volume} \times 100$

[3] $\frac{[Protein]\ Hydroxylapatite\ Pool\ I}{[Protein]\ Sample} \times \frac{\%\ Yield\ HBsAg}{100}$ Analyses of samples for contaminants by immunoelectrophoresis (FIG. 8) showed a very weak precipitin line in fraction I, a stronger line in fractions II to VI and a heavy broad line in the pooled fraction VII–VIII all migrating between the alpha$_2$ and albumin regions.

Electron microscopy of samples showed mostly spherical particles of 22 to 28 nm in diameter in fractions I to III, spherical particles and filaments in fractions IV to VI, mostly small spherical particles and a few filaments in fraction VII and VIII.

The concentrated samples from the previous step were submitted to complete purification by density gradient centrifugation under the conditions described under Methods.

Figure 9:
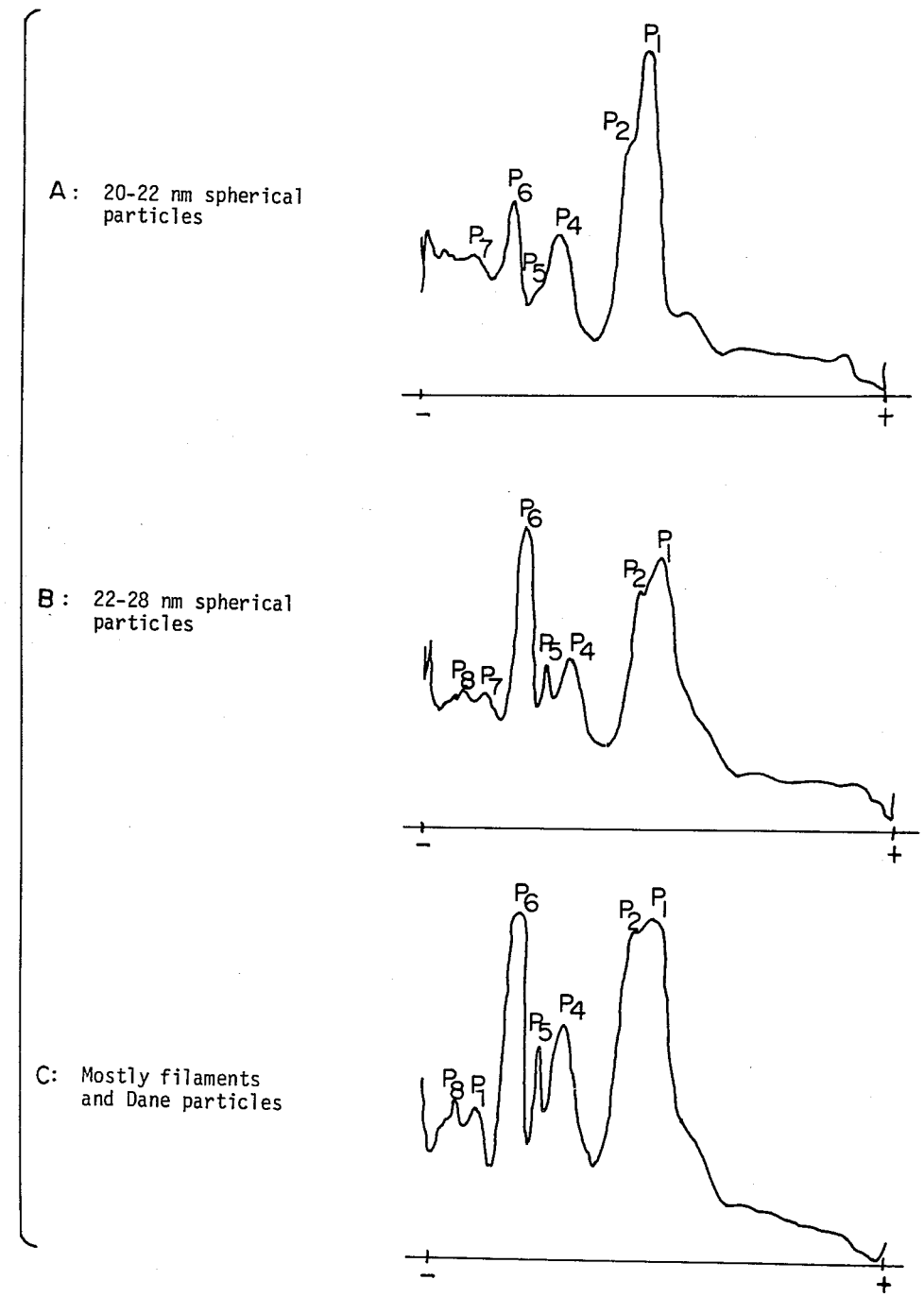
FIG. 9 shows the results of polyacrylamide gel electrophoresis of purified preparations of HBsAg/e subjected to Coomassie blue staining. The samples were run in a 7.5% SDS-acrylamide gel under the conditions described above. The gels after Coomassie blue staining were scanned in a Joyce-Loebl microdensitometer:
  A: 20—22 nm spherical particles of HBsAg
  B: 22—28 nm spherical particles of HBsAg
  C: HBsAg/e particles composed mostly of filaments and Dane particles.

Purified preparations of HBsAg composed mostly of 20–22 nm spherical particles, 22–28 nm spherical particles, variable size filaments and Dane particles, each containing 100 μgm of protein were analyzed for polypeptide composition by polyacrylamide gel electrophoresis (FIG. 9). Apparent quantitative differences can be observed in protein peaks of individual samples. Further differences are found in the peak 5 which shows only as a small shoulder in the preparation of 20–22 nm particles (FIG. 9A) but it is distinct in the preparation of 22–28 nm particles (FIG. 9B) and in the sample containing mostly filaments and Dane particles (FIG. 9C). Aliquots of 20–22 nm (FIG. 10A) and 22–28 nm spherical particles (FIG. 10B) run in parallel to the above samples were tested for carbohydrates by Schiff base staining. It is evident that peaks $P_1$, $P_2$, $P_4$ and $P_6$ contain carbohydrates.

The low molecular weight carbohydrate peaks (on the right of FIG. 10) probably represent glycolipids since they do not show by Coomassie blue staining. The approximate molecular weights of the polypeptides are presented in Table 6.

TABLE 6

| | MOLECULAR WEIGHT ($\times 10^3$) OF POLYPEPTIDES OF HBsAg/e PARTICLES SUBTYPE* adwx | | | | | | | | |
|---|---|---|---|---|---|---|---|---|---|
| Peak Number | P1 | P2 | P3 | P4 | P5 | P6 | P7 | P8 | P9 |
| Chimpanzee HBsAg/e | 23–24 | 26–27 | — | 44–45 | 55 | 68–69 | 103–105 | 108–110 | 115–118 |

A vaccine is prepared from the large particle fractions obtained above by addition of human serum albumin at 0.5 mg/ml followed by inactivation serially by cobalt irradiation (2.5 million rads) formalin inactivation using conventional procedures (37° C., 96 hours 1:2,000 concentration) followed by use of β-propiolactone using conventional procedures as in rabies vaccine manufacture.

EXAMPLE 2: A MODIFIED IMPROVED PEG PROCEDURE FOR ISOLATION OF HBsAg/e

A modified procedure for PEG precipitation was applied to 2.6 liters of pooled HBsAg containing plasma from a single carrier chimpanzee containing e-antigen in an uncombined, unprecipitated form. The plasma was adjusted approximately to pH 4.6 and immediately a 30% solution of PEG was added to a final concentration of 2%. The solution was chilled on ice for 30 minutes (instead of overnight at 4° C. as in the previous example), and the precipitate was removed by centrifugation.

The supernatant, containing the HBsAg, was brought to a PEG concentration of 4% (instead of 4.5% as in the previous example) by addition of 6.6 parts per 100 of a 30% solution of PEG at room temperature. The suspension was again chilled on ice for about 30 minutes and the precipitated HBsAg/e was removed by centrifugation. The precipitate was resuspended to 200 ml in distilled water. The bulk of PEG and some accompanying contaminants were removed by adjusting the pH to 5.0, chilling the solution on ice for 30 minutes, and removing the resultant precipitate by centrifugation. The pH of the clear supernatant from the previous step was readjusted to 4.6 and 30% PEG was added to a final concentration of 3% (instead of 4.0–4.5% as previously employed). The material was again chilled on ice for about 30 minutes and the precipitate of HBsAg/e was removed by centrifugation.

The precipitate from the previous step, containing HBsAg/e, was suspended in 100 ml distilled water. The bulk of the PEG was precipitated by again adjusting the pH to 5.0. After overnight storage at 4° C. the suspension was clarified by centrifugation. To the clear supernatant, containing HBsAg/e, 0.5 M sodium phosphate buffer pH 7.2 was added to a final concentration of 0.02 M and the final volume was adjusted to 120 ml with distilled water.

The results of this purification, summarized in Table 7, show more than 33 fold purification of HBsAg (against 24 fold purification in the previous procedure)

TABLE 7

| PURIFICATION OF HBsAg BY PEG 6000 PRECIPITATION | | | | | |
|---|---|---|---|---|---|
| SAMPLE | VOLUME (ml) | HBsAg 1/CEP TITER | TOTAL PROTEIN (g)[1] | PERCENT YIELD HBsAg[2] | FOLD PURIFICATION[3] |
| Original Plasma | 2600 | 80 | 130.0 | 100.0 | 0.0 |
| First 4% PEG Precipitate | 1200 | 160 | 22.8 | 92.3 | 5.3 |
| Second 3% PEG Precipitate | 120 | 1600 | 3.6 | 92.3 | 33.3 |

[1] Kjehldahl

[2] $\frac{[HBsAg] \text{ sample} \times \text{Volume}}{[HBsAg] \text{ plasma} \times \text{Volume}} \times 100$

[3] $\frac{[Protein] \text{ plasma}}{[Protein] \text{ sample}} \times \frac{\text{Percent Yield HBsAg}}{100}$ The factors which contribute to the improved procedure (example 2) are:

1. Chilling of solutions on ice for 30 minutes instead of overnight shortens the purification to one working day as compared to several days in the method of example 1.
2. Shortening the time of cooling leads to more specific precipitation of HBsAg/e and less contamination with plasma proteins.
3. Reducing the volume of sample after the first precipitation of HBsAg/e requires smaller volumes of PEG for selective precipitation in subsequent steps, and allows the second precipitation at pH 5.0 to remove the bulk of PEG from the sample.

Vaccine containing albumin is produced by the inactivation steps of Example 1.

EXAMPLE 3: FRACTIONATION OF HBsAg/e BY BATCHWISE TREATMENT WITH HYDROXYLAPATITE.

The resuspended PEG precipitate of HBsAg/e was (example 2) treated batchwise with hydroxylapatite instead of by the column chromatography procedure. A 500 ml volume of packed hydroxylapatite (Bio-Rad Labs) was suspended in 800 ml of 0.02 M sodium phosphate buffer pH 7.2, and, after addition of the above preparation of HBsAg/e, was stirred on a magnetic stirrer for 30 min. at room temperature. The slurry was divided into two equal aliquots and centrifuged in 1 liter buckets in the Sorvall RC-3 centrifuge at 4,000 rpm for 10 min. The supernatant was decanted and the sediment was successively washed with 1 liter each of 0.02 M and 0.05 M sodium phosphate buffer pH 7.2. The eluates were pooled, concentrated by ultrafiltration using a PM-30 membrane ad diafiltered with 0.02 M phosphate buffer of pH 7.2, 0.02% NaN₃, and adjusted to 60 ml with the same buffer.

The concentrated sample was further purified by rate zonal centrifugation in a discontinuous sucrose gradient.

The separated HBsAg/e particles were pooled into three fractions, dialyzed and concentrated by ultrafiltration as described above. The samples studied by electron microscopy showed mostly large filaments and Dane particles in Fraction I (FIG. 11a); filaments, Dane particles and 22–28 nm spherical particles in Fraction II (FIG. 11b) and 20–28 nm spherical particles in Fraction III (FIG. 11c).

Batchwise treatment of the resuspended PEG precipitate of HBsAg/e has the advantage over column chromatographic procedures described previously, in that fractionation is realized within a day as compared to five days required for elution by colum chromatography. The vaccine is prepared by the procedures of Example 1 using albumin and the stated inactivation procedures.

EXAMPLE 4: DISAGGREGATION OF HBsAg/e PARTICLES WITH IONIC AND NONIONIC DETERGENTS.

HBsAg/e particles were treated at room temperature (for 5 min to 2 hours) with the following detergents: 0.5–2% Nonidet NP-40 (a detergent) (Shell Oil Co.), 0.5–2% Tween 80 (surfaceactive agent), 5–10% Triton X-100 (organic surface-active agent), 0.1–1.0% sodium dodecylsulfate, etc. The objectives were: (1) potentiation of antigenic activity in detergent treated samples, and (2) inactivation of infectivity of the samples.

The optimal conditions of treatment were determined by analyses of samples before and after detergent treatment using thin layer isoelectric focusing. Individual components of disaggregated samples can be isolated using various separation techniques. For example, molecular exclusion, adsorption and ion exchange chromatography ultracentrifugation techniques, various methods of electrophoresis, etc. One of the highly efficient techniques is the method of zone convection isoelectric focusing described below.

Isoelectric Focusing

Thin layers were formed of Sephadex G-75 gell cellulose support, sold by Pharmacia, Uppsala, Sweden in a 1% solution of pH 4.0–6.0 or pH 3.5–10.0 ampholine according to the method of Radola. The plates were run in an LKB multipore apparatus. Prints were taken into Whatmann 3MM chromatography paper. Prints were divided along the line of separated samples and cut into 0.5 to 1 cm. zones. The individual zones were further cut into smaller pieces, moistened with 0.2 ml. of buffered saline and eluted with 0.2 ml. of normal (free of HBsAg and anti-HBs) human serum. A 200 ul aliquot from each eluate is used for radioimmunoassay. The strips between the separated samples are also cut, eluted with 0.4 ml of degassed distilled water and used for pH measurements. When two prints were taken, the first one was used for protein staining and the second was cut for HBsAg radioimmunoassay and pH measurements. An aliquot from each sample is treated with 5 to 10% of a nonionic detergent (Triton X-100) for at least 20 minutes at room temperature before application to the gel and run under the above described conditions in comparison to a sample which has not been treated with detergents.

Zone Convection Isoelectric Focusing

An apparatus was constructed from lucite on the principles described by Valmet (U.S. Pat. No. 3,616,456). It consisted of 32 compartments of 50 ml total volume. Certain modifications leading to improvements were introduced. The trough was filled with 50 ml. of solution containing 1% ampholine (LKB) of the desired pH range and 10% glycerol. The solution in compartments No. 4, 5 and 6 (counting from the anode) was replaced with 1.5, 3.0 or 4.5 ml. of the sample containing 1% ampholine and 10% glycerol. Electrofocusing was fun at 1,000–1,500 V for four days at 4° C. The fractions were separated from the individual compartments after removing the lid, clarified by centrifugation, and analyzed for proteins by measuring O.D. at 280 nm., and for HBsAg by RIA and for pH.

Analysis of Triton X-100 Treated Preparations of HBsAg/e

Fractions of HBsAg/e particles isolated by column chromatography on hydroxylapatite (FIG. 4) were analyzed by thin-layer isoelectric focusing under the conditions described above. A preparation composed mostly of 22–28 nm. spherical particles (FIG. 12A) and a heterogenous mixture consisting mostly of larger particles (filaments, Dane particles) (FIG. 12B) showed a relatively low degree of heterogeneity in the surface charge of the particles. A main peak of antigenic activity was found at pH 4.8 and two minor peaks of activity were observed at pH 4.0–4.1 and pH 4.4–4.6. The samples after Triton X-100 treatment showed a two-fold enhancement of antigenic activity determined by planimetry (FIG. 13). The enhancement of activity in other experiments varied from 2–8 fold. Other than some residual antigenic activity observed in the original low pH region (pH 4.1–5.0) the main peaks of antigenic activity were found at a higher pH range of 5.3 and 5.8 to 5.9 and a minor peak at pH 7.1–7.2. E-antigen activity was found only in the pH region 5.6–7.4. This antigen was found in this region by the insensitive agar gel diffusion test. Thus the quantity of e-antigen in this region is clearly high. Indeed the radioimmunoassay peak at this region could represent contamination of the $^{125}$I-"Anti-HBs" used in the Ausria technique (Abbott Laboratories) by a very small quantity of anti-e.

Thus disaggregation of HBsAg/e by non-ionic detergent Triton X-100 leads to potentiation of antigenic activity. This has an obvious advantage for preparation of antigenic material for active immunization. A further advantage of detergent dissociation is the fact that this results in physical dissociation of the HB particles. Few if any particles survive intact after treatment with Triton X-100 under the conditions described. This in itself is therefore an important step in the inactivation of infectivity. Furthermore, if desired, this step can be combined with procedures such as precipitation with anti-HBc antibody, and/or Deoxyribonuclease treatment, to remove all HBV associated genetic material from the vaccine. This may prove desirable because of the (theoretical) possibility of oncogenicity.

This experiment thus reveals one method to purify e-antigen from HBsAg/e associated particles by a combination of Triton X100 dissociation and zone convection isoelectric focusing. As equipment is now available (Roche Institute) for carrying out this technique on a multiliter scale, the approach described is suitable for preparation of an e-antigen containing vaccine which is essentially free of conventional HBsAg. Such a vaccine has obvious advantages as indicated above.

The final vaccine product is produced by the procedure of Example 1 using human albumin and the stated inactivation procedures upon the desired fraction after detergent association.

EXAMPLE 5: PURIFICATION OF SOLUBLE e-ANTIGEN FROM PLASMA OF HBsAg/e CHRONIC CARRIERS FOR USE AS A VACCINE

Figure 2:
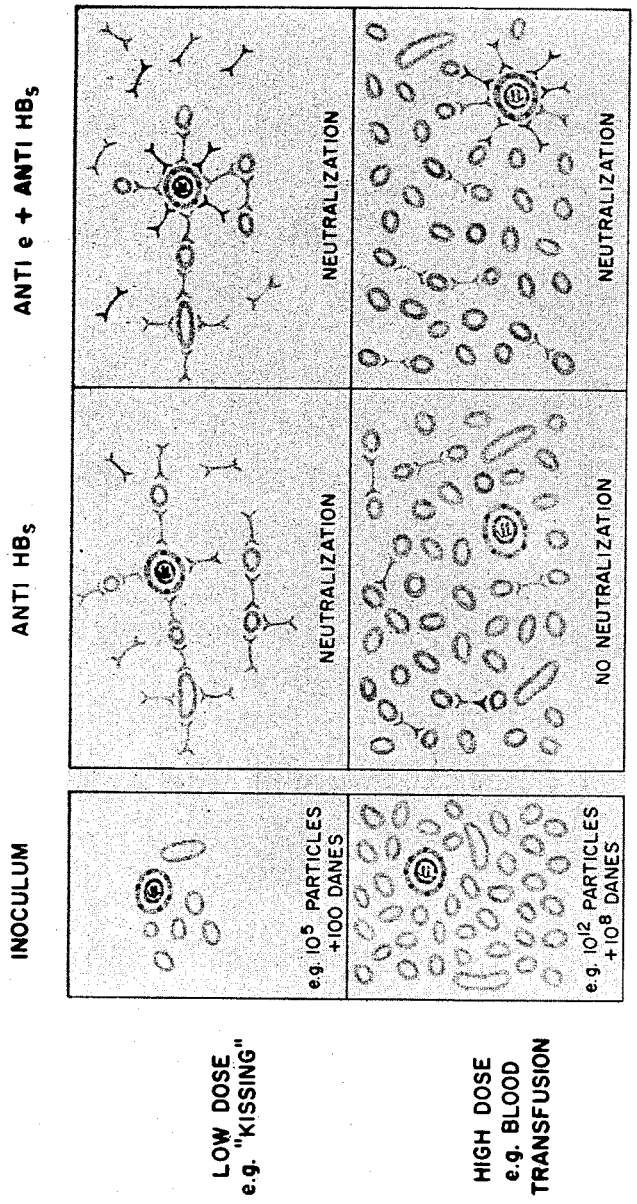
FIG. 2 graphically shows the differential effects of antibodies of e-antigen and antibodies of hepatitis B surface antigen in the neutralization of Dane particles as a function of exposure dose. From this it is seen that the antibodies generated from a HBsAg vaccine free of e-antigen are insufficient to effect total neutralization of the antigen containing sites. However, where a high dosage of antigen is involved, the antibodies generated from a vaccine characterized by the addition of e-antigen are sufficient to neutralize virtually all of the antigen sites, thereby indicating that the presence of e-antigen in a vaccine materially affects the extent to which neutralization of all antigens takes place.
Figure 3:
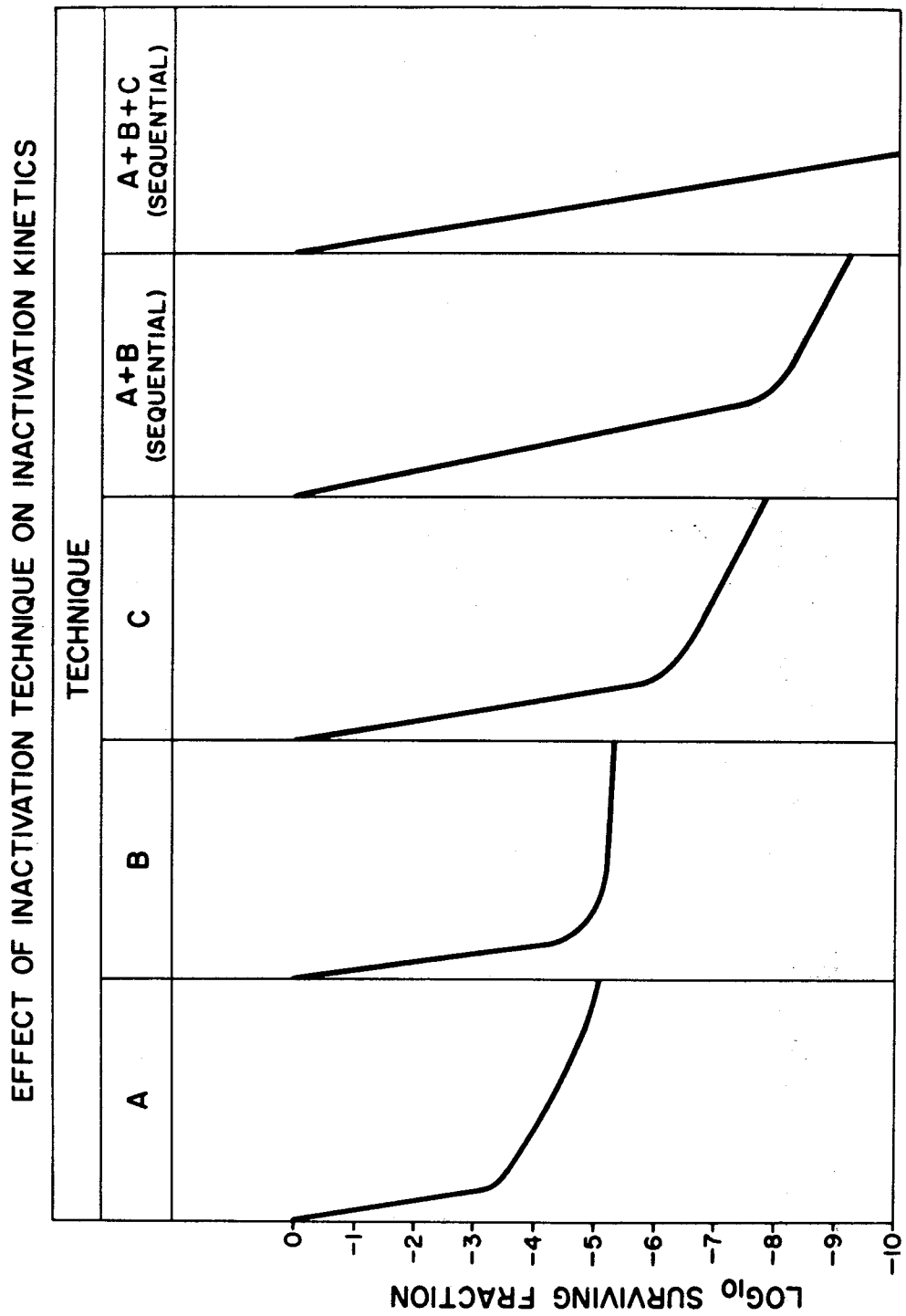
FIG. 3 graphically illustrates the fact that with any given inactivation procedure a minor proportion of the infectious virus will be resistant to inactivation. However, when different inactivation techniques are employed sequentially, these resistant fractions can be inactivated.

As indicated above (see FIG. 2) HBsAg/e positive plasma contains e-antigen in a soluble (i.e. non particle associated, or MW <1,000,000) form. Indeed this form predominates in many such plasmas, and therefore can provide an ideal source of e-antigen for immunization.

The properties of soluble e-antigen have been determined by Magnius, Ohori and ourselves in a preliminary manner as follows: density (CsCl) 1.28–1.29; $S_{20,w}$ = 11.6; Molecular weight = 150,000–900,000; Isoelectric point 5.5–6.6; elution from diethylaminoethyl cellulose at 0.15 M NaCl.

On the basis of these and other properties the following purification method has been developed:

1. HBsAg/e plasma is first fractionally precipitated by PEG 6000 with removal of HBsAg associated particles and some serum proteins by precipitation with 5–9%, preferably 8% w/y, PEG 6000 at pH 7.0, 20° C., followed by precipitation of e-antigen and some plasma proteins with PEG at 9–13% PEG concentration. Variations of the details of fractional precipitation, e.g., in pH, temperature, PEG concentration, as well as use of the pH 5.0 precipitation step to remove PEG, can also be used.

2. The PEG precipitate is resuspended in distilled watter (1/10 volume) or suitable buffer and subjected to isoelectric focusing in 10% glycerol, containing 1–2% ampholytes of pH range 3.5–10.0.

3. The e-Ag peak is pooled, diafiltered on an Amicon PM 30 filter vs 0.05 M phosphate buffer, 0.01 M Triton X 100 pH 7.6, and applied to a DEAE cellulose column equilibrated with the same buffer. Elution is performed with a linear gradient of 0.0–0.5 M NaCl in the same buffer. E-Ag is eluted at about 0.15 M NaCl in a high state of purity.

4. After concentration by diafiltration as before, remaining impurities are removed, if desired by rate zonal centrifugation in 10–30% sucrose gradient, or equivalent density gradient, with recovery of the 11.6 s peak.

5. Purified e-Ag is stabilized by addition of human serum albumin to a concentration of Ca 0.5 mg/ml. The concentration and nature of colloid stabilizer is of course not critical.

Such preparations, at a concentration of about 20 μgm per dose, may be used instead of the particulate of HBsAg/e vaccine, subject to the use of inactivation and sterilization steps as described herein, for preparation of the HBsAg/e particulate vaccine.

Application Ser. No. 426,825 referred to hereinabove is assigned to the assignee of this present application.

What is claimed is:

1. An antigenic composition against viral hepatitis comprising:
    A. Antigenic particles having a particle size in the range of 30 to 50 nm, said antigenic particles containing unprecipitated free hepatitis B surface antigens,
    B. Said antigenic composition having less than 10 units of antibodies of heptatitis B surface antigens per 1,000 units of heptatitis B surface antigen,
    C. At least 5% of the particles of said antigenic composition in the size range of 30 to 50 nm containing unprecipitated e-antigen,
    D. Said HBsAg and said e-antigen being present in said antigenic composition in an amount sufficient to produce antibodies when introduced into a host animal, the balance being a medium which is physiologically acceptable.

2. An antigenic composition according to claim 1 characterized in that at least 1.0% of said particles of 30 to 50 nm in size contain deoxyribonucleic acid (DNA).

3. An antigenic composition according to claim 1 wherein said particles of size 30 to 50 nm comprise:
    (a) filamentous proteinaceous particles of an elongated shape having a diameter of 20 to 50 nm; or
    (b) Dane particles having a particle size of between 40 and 50 nm.

4. An antigenic composition according to claim 3 wherein said antigenic composition comprises a mixture of said filamentous particles and said Dane particles:

5. An antigenic composition according to claim 3 containing soluble, free and non-precipitated e-antigen in said physiologically acceptable medium, said soluble e-antigen being characterized by a density of 1.27–1.29 g/cc; and a molecular weight of 50,000–900,000.

6. An antigenic composition according to claim 3 containing HBsAg containing spherical particles of particle size of 25 to 50 nm.

7. An antigenic composition according to claim 1 characterized by particles containing DNA and hepatitis B core antigen.

8. An antigenic composition according to claim 3 containing between 1.0 and 25% Dane particles based on differential counts using electron microscopy.

9. An antigenic composition according to claim 3 containing between 1.0 and 50% of filamentous particles based on differential counts using electron microscopy.

10. An antigenic composition according to claim 3 having a density of between 1.23 and 1.34.

11. An antigenic composition according to claim 3 having detectable free, unprecipitated and uncombined e-antigen detectable by the agar gel diffusion technique.

12. An antigenic composition according to claim 1 which when used in chimpanzees in accordance with the recommended immunization schedule results in an anti-HBs titer of at least 1:100 by passive hemagglutination test, which anti-HBs remains detectable at a titer of at least 1:10 for 1 year.

13. An antigenic composition against viral hepatitis comprising:
    A. Antigenic particles having a particle size in the range of 30 to 50 nm, said antigenic particles containing unprecipitated free hepatitis B surface antigens,
    B. Said antigenic mass having less than 10 units of antibodies of hepatitis B surface antigens per 1,000 units of heptatitis B surface antigen,
    C. At least 5 percent of the particles of said antigenic mass in the size range of 24 to 50 nm containing unprecipitated e-antigen,
    D. Said e-antigen being present in said antigenic mass in an amount sufficient to produce antibodies when introduced into a host animal, the balance being a medium which is physiologically acceptable.

14. An antigenic composition according to claim 13 containing soluble, free and non-precipitated e-antigen in said physiologically acceptable medium, said antigenic composition being characterized by a density of 1.23–1.34 g/cc.

15. An antigenic composition according to claim 13 having detectable free, unprecipitated e-antigen detectable by electron miscroscopy.

* * * * *